United States Patent [19]

Zebrack

[11] Patent Number: 4,738,262

[45] Date of Patent: Apr. 19, 1988

[54] THERAPEUTIC WEIGHT DISPERSING SHOE SOLE

[76] Inventor: Samuel D. Zebrack, 6045 Hampton, St. Louis, Mo. 63109

[21] Appl. No.: 19,686

[22] Filed: Feb. 27, 1987

[51] Int. Cl.⁴ .......................... A61F 5/14; A43B 7/14
[52] U.S. Cl. .................................. 128/581; 128/586; 128/615; 36/116
[58] Field of Search ................. 128/615, 581, 582–586, 128/589, 590, 607, 610, 613, 614, 617, 621, 623; 36/114, 127, 116, 122, 115, 116

[56] References Cited

U.S. PATENT DOCUMENTS

| | | | |
|---|---|---|---|
| 460,523 | 9/1891 | Critchlow | 36/59 R |
| 665,797 | 1/1901 | Newton | 36/59 R |
| 1,360,995 | 12/1920 | Anderson | 36/116 |
| 1,776,750 | 9/1930 | Burns | 128/586 |
| 1,870,751 | 8/1932 | Reach | 36/127 |
| 2,134,598 | 10/1938 | Barns | 128/586 |
| 2,522,515 | 9/1950 | Hill | 128/615 |
| 2,691,832 | 10/1954 | Lurie | 128/586 |
| 2,769,252 | 11/1956 | Monier | 128/581 |
| 2,932,910 | 4/1960 | Brown | 36/122 |
| 3,807,061 | 4/1974 | Krus et al. | 36/114 |
| 4,468,870 | 9/1984 | Sternberg | 36/127 |
| 4,628,936 | 12/1986 | Langer et al. | 128/614 |

FOREIGN PATENT DOCUMENTS

| | | | |
|---|---|---|---|
| 306632 | 7/1918 | Fed. Rep. of Germany | 128/581 |
| 1137347 | 9/1962 | Fed. Rep. of Germany | 128/581 |
| 2834814 | 2/1980 | Fed. Rep. of Germany | |
| 2511850 | 3/1983 | France | 36/114 |
| 52732 | 1/1911 | Switzerland | 36/122 |
| 219403 | 6/1942 | Switzerland | 128/581 |

OTHER PUBLICATIONS

Hampton, G. H., "Therapeutic Footwear for the Insensitive Foot", Physical Therapy, vol. 59, No. 1, Jan. 1979, pp. 23–29.

Primary Examiner—Charles Pearson
Assistant Examiner—Tonya Lamb
Attorney, Agent, or Firm—Haverstock, Garrett and Roberts

[57] ABSTRACT

There is described a novel therapeutic weight dispersing shoe sole having an extended width sole surface under the forward half of the foot with skates along both the medial and lateral extensions of such extended sole and preferably with an added heel lift. The therapeutic weight dispersing shoe sole has been found to reduce pressure exerted in a limited area of the plantar surfaces of the foot and to be especially useful for wearers subject to insensitivity of the feet.

11 Claims, 1 Drawing Sheet

U.S. Patent
Apr. 19, 1988
4,738,262
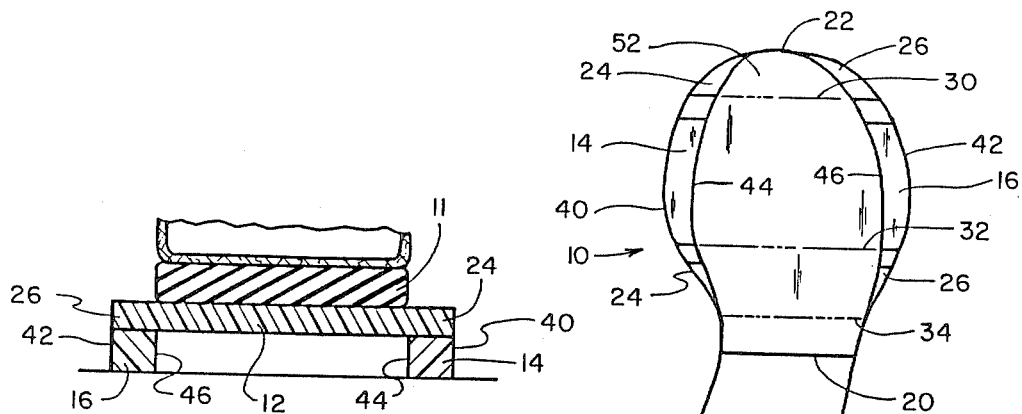
Fig. 3
Fig. 1
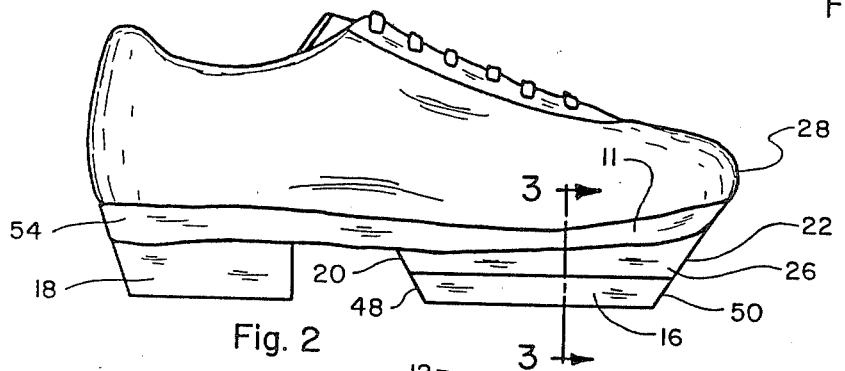
Fig. 2
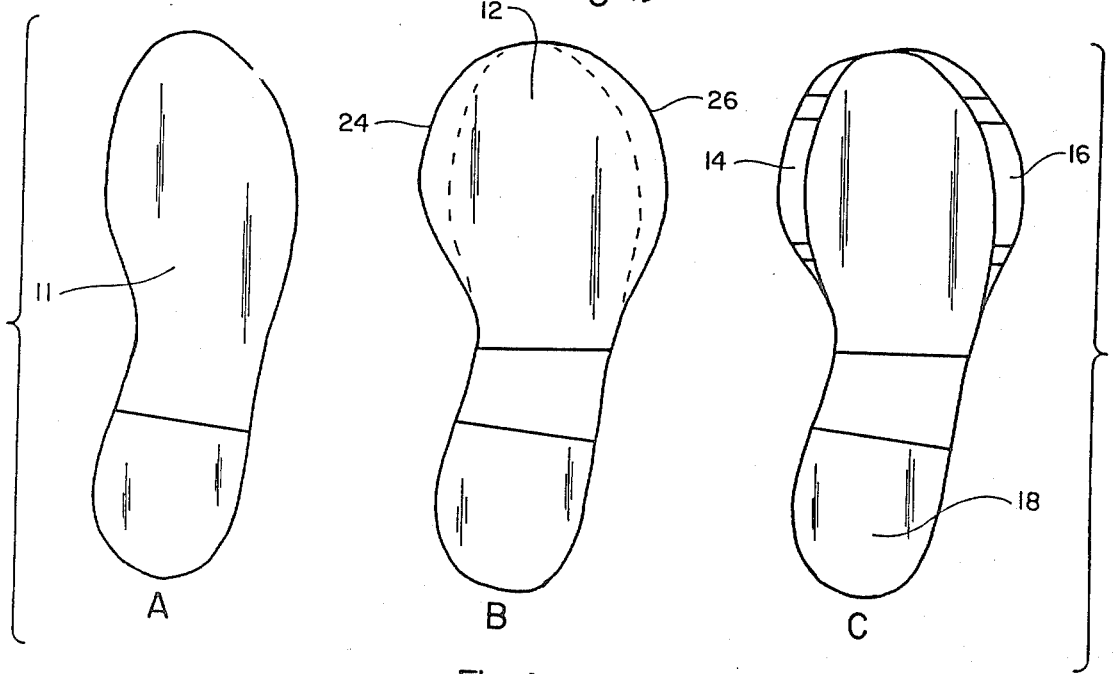
Fig. 4

THERAPEUTIC WEIGHT DISPERSING SHOE SOLE

This invention relates to a therapeutic shoe sole, and more particularly, to a sole for use on a shoe to be worn by persons with insensitive feet or who experience abnormal pressures on the feet.

BACKGROUND OF THE INVENTION

A number of medical conditions can produce a loss of nerve sensation in the extremities such as the hands and feet of normally active persons. These include, among others, diabetes, nerve injury, spina bifada, Hansen's disease, syringomyelia and peripheral neuritis. In many cases the most easily noted locale of such insensitivity or loss of nerve sensation occurs in one or both feet of an individual. When such insensitivity occurs the normal sensations of discomfort or pain are not present and the individual can incur damage to the soft tissues of the foot due to prolonged pressure, rubbing, or other condition caused by walking, standing or other movement, particularly in tight or ill-fitting shoes. This damage to the feet is particularly prevalent in persons who have developed diabetes, but are still normally active individuals and if not treated early can result in rupturing of the skin or ulceration of the soft tissues of the foot.

Other persons can also incur abnormal pressures on the tissues of the feet as a result of a variety of conditions, such as prolonged standing or walking, job stresses, deformations of the arches of the feet, birth defects and traumatic injuries.

A variety of treatments for the prevention of such conditions have been developed which vary in their effectiveness. The more successful have involved additions to or redesign of footwear for use by persons with such insensitivity of or abnormal pressures on the feet. Added soft padding, and particularly, energy-absorbing insoles are most frequently used. In addition, some added modifications to the soles of shoes have been suggested, such as, metatarsal bars, rocker bars or wedges and, in case of deformed feet or extreme pressure conditions, alterations such as rocker soles or the like are prescribed. These latter alterations of the shoe are designed to co-exist with changes in the gait or stride of the person when walking. All of such expedients basically aim at reducing the concentration of pressure forces on areas of the plantar surface of the foot, and limiting the lift-off of the heel so less pressure is imposed on the forefoot.

Accordingly, the present invention is concerned with providing a shoe sole which provides for the redistribution and relief of excessive pressure conditions which frequently occur from walking or standing in daily activities or by persons with insensitive feet and particularly persons suffering from diabetes or one of the other conditions mentioned above. The present invention provides a sole structure for shoes which functions when walking in such a way as to reduce the total pressures imposed on the plantar surface of the forefoot and therefore to lessen the time such pressures are imposed on the metatarsal heads and on the plantar surfaces of the phalanges during walking. The present invention therefore represents a substantial improvement in shoe soles for active individuals and those with insensitive extremities and overcomes many of the disadvantages and shortcomings of previously known shoe soles intended for such purposes.

SUMMARY OF THE INVENTION

The present invention is embodied in a novel therapeutic weight dispersing shoe sole having an extended width sole surface under the forward half of the foot and with skates along both the lateral and medial extensions thereof and/or in conjunction with added heel height. The novel sole has been found to reduce pressures exerted on a limited area by distributing such pressures over wider areas and at the same time to delay and reduce the total time that the metatarsal head area and the phalanges are subjected to pressure during each step. Overall the improved therapeutic weight dispersing shoe sole has been found to relieve pressure and tenderness of the plantar surfaces of the foot of persons having diabetes-related loss of sensitivity of the feet or avert stress symptoms associated with constant standing.

A principal object of the present invention is to provide an improved therapeutic weight dispersing shoe sole for relieving pressures on the foot.

Another object of the present invention is to provide a therapeutic weight dispersing shoe sole which will reduce the incidence of pressure and stress on the insensitive foot.

A further object of the present invention is to provide a therapeutic weight dispersing shoe sole which will aid in the recovery from pressure ulcerations of the insensitive foot.

A still further object of the present invention is to provide a therapeutic weight dispersing shoe sole that is relatively economical to produce and incorporate in shoes.

These, as well as other objects and advantages of the present invention, will become apparent after considering the following detailed description of the preferred embodiment with the accompanying drawings.

BRIEF DESCRIPTION OF THE DRAWING

FIG. 1 is a bottom plan view of a therapeutic shoe sole for a left shoe constructed in accordance with the present invention;

FIG. 2 is a side elevation view of a right shoe with the sole of FIG. 1 in place;

FIG. 3 is a front sectional view of the shoe and sole of FIG. 2 taken along the line 3—3 of FIG. 2; and FIG. 4 is a progessive three-part bottom plan view showing the manner of incorporating the shoe sole of FIG. 1 onto a shoe.

DESCRIPTION OF THE PREFERRED EMBODIMENT

The therapeutic weight dispersing shoe sole of the present invention comprises a sole for addition to an existing shoe having three portions or elements characterized by the location thereof, and which portions or elements act cooperatively to produce the desired results. Referring to FIGS. 1 and 2, by reference numbers, wherein like numbers refer to like elements, the elements which comprise the new therapeutic weight dispersing shoe sole are: (a) an extended width sole element 12, (b) two skate elements 14 and 16 positioned below both the medial and lateral extensions 24 and 26 of extended sole element 12 and an added heel lift element 18.

Extended width sole element 12 is to be positioned under at least the front portion of the original shoe sole 11 and extends longitudinally from its rearward end 20 positioned beneath and at least slightly posteriorly of the metatarsal heads area of the foot to its forward end 22 at the front of the existing shoe sole 11. Laterally extended width sole 12 gradually increases in width from that of the original sole 11 at the toe 28 of shoe 10 to its full width at a point 30 about the area of the proximal middle phalangeal articulation, generally about 1½ to 2 inches from the front or apex 28 of the toe of the shoe upper. The full width of the sole extensions 24 and 26 are each about ½ inch (1.25 cm.) greater than the width of the original sole 11 at a corresponding point along the side of extended sole 12, which full extensions are maintained rearwardly at least to a point 32 below the metatarsal-phalangeal articulation. The widths of the extensions 24 and 26 from point 32 gradually narrow until they again coincide with the contours of original sole 11 at a point 34 at least slightly posterior of the metatarsal heads area of the foot.

The skate elements 14 and 16 which can be integrally molded together with extended sole element 12, are located on extended sole element 12 below the medial and lateral extensions 24 and 26 and are generally coextensive with the widest portions of the extensions. Skate elements 14 and 16 are thus positioned beneath the proximal middle phalangeal articulation area, the metatarsal-phalangeal articulation and the metatarsal heads or proximal metatarsal articulation area. The skate elements 14 and 16 are approximately the width of sole extensions 24 and 26, i.e. appoximately ½ inch at the widest point thereof, and can range in thickness from about the thickness of the extended width sole element up to 50% greater in thickness. The relative thicknesses and location of the skate elements 14 and 16 to the extended sole element 12 and original shoe sole 11 may be seen in greater detail by reference to FIGS. 2 and 3. The outer sides 40 and 42 of both the medial skate element 14 and lateral skate element 16 follow the contours of the sides of the extended width sole element 12, while the inner sides 44 and 46 of skate elements 14 and 16 substantially follow the lines of the sides of the original shoe sole.

To diminish the effect on the gait of the wearer the rearward end 48 of the lateral skate element 16 is preferably tapered while forward end 50 is likewise tapered to rejoin the level of extended sole element 12 as shown in FIG. 2. The ends of the medial skate element 14 are correspondingly tapered. The taper of the rear ends of the skate elements are preferably at an angle of from about 35° to about 60° to the horizontal. The rear edge 20 of extended sole element 12 can also be tapered, if desired, to about the same angle as the rear ends of skate elements as likewise shown in FIG. 2. To aid in the lift-off phase of the gait during walking it is desirable to taper the forward end 50 of the lateral skate element 16 and the forward end of the medial skate element 14 at a somewhat lower angle of from about 20° to about 35° to the horizontal to rejoin the forward portion 52 of extended sole element 12. For the same reasons it is preferable to provide a very gradual taper to the forward end portion 52 of extended sole element 12 forward of the skates to a thickness at the forward end 22 thereof of from about ¼ to ½ the thickness of the rest of extended sole element 12, i.e. the thickness of the main or central portion thereof (not shown).

The heel lift element 18 positioned below the original heel portion 54 of original shoe sole 11 can be varied in thickness as desired to produce a greater or lesser effect on the supination of the foot and the gait of the wearer. Thus, the heel lift element 18 can be of a thickness approximately equal to the total thickness of extended sole element 12 and the skate element 14, as shown in FIG. 2. Heel lift element 18 alternatively can be only the thickness of the extended sole element 12, or even less, if desired. In some cases it may even be advantageous to eliminate the heel lift element 18 entirely, but the wearer's gait will be more severely affected as a result.

FIG. 4 serves to illustrate the manner in which the various elements can be separately assembled onto the sole 11 of an existing shoe shown at A. At B there is shown the extended width sole element 12 having medial and lateral extensions 24 and 26 fixed to the bottom of sole 11. At C there are shown medial skate element 14 and lateral skate element 16 mounted below and fixed to sole extensions 24 and 26 and heel lift element 18 fixed below the original heel portion 54 of shoe sole 11. As more fully described below, these means may be fixed to the original sole 11 and extended sole 12 respectively by use of adhesives and/or other fixing means, or preferably, they can be produced as one or two unitary structures.

In many types of shoes it will be most convenient and economical to produce the heel lift element 18 and extended width sole element 12 as a single structure and such is contemplated. Likewise, it will be appreciated that for reasons of economy and ease of production the extended width sole element 12 and the skate elements 14 and 16, with or without heel lift element 18, can also be formed as a unitary article. This is particularly true when the materials from which the therapeutic weight dispersing shoe sole of this invention is formed are relatively springy, elastic or energy-absorbing materials, such as so-called crepe rubber or polymer compositions and expanded or foamed compositions, since these materials are most readily formed by molding operations producing one-piece articles. Alternatively, and particularly when harder, more traditional materials are used, such as leather or unexpanded polymer compositions, the three elements can be formed as separate parts and thereafter joined by means to fix them together. In the instance of use of polymer or expanded compositions this is usually by means of adhesives, but in other cases can utilize both adhesives and nails or stitching as well. Any of such well-known means to fixedly join sole and heel structures to shoe structures can be used.

When worn by a subject the therapeutic weight dispersing shoe sole of the present invention works in at least three ways to relieve and reduce the imposition of concentrated pressures on the plantar surfaces of the wearer's foot. First, the expanded width sole element 12 acts to distribute the vertically imposed pressures of the walker's weight over a larger surface area, and thus reduces the pressures over a single small area. Second, the skate elements 14 and 16 provide two added rays for the transfer of walking forces in addition to the metatarsal bones of the foot, which may be considered as five rays, and as the wearer takes steps, thus distribute these forces over more points. Third, the skate elements 14 and 16 serve to delay and diminish the time during which the metatarsal heads of the foot are subjected to the forces and stresses of walking. It has long been known that the weight and walking stresses imposed by each step originate upon heel contact and are transmitted along the lateral border of the foot from the heel to the fifth metatarsal head, then across the metatarsal heads and out into the great toe and other toes from he metatarsal heads. By delaying the time of the transfer of forces across the metatarsal heads by the interposition of the added extended skate elements, the total of such forces over the time of each step are reduced and, hence, the result of such forces as pressures on the plantar surfaces beneath the metatarsal heads and each toe is diminished. This results in less incidence of reddening, swelling and pressure sores and eventual potential ulceration of the soft tissues lying interiorly of the plantar skin surfaces of the foot. Such a result is of particular importance to normally active persons who experience insensitivity of the feet.

It has been found in practice that wearers of shoes fitted with the therapeutic weight dispersing shoe sole of the present invention who suffer from insensitivity of the feet due to a diabetic condition experience significantly reduced incidence of redness, swelling and pressure as the result of walking when wearing shoes fitted with the soles described herein. In certain instances recovery of a person from an ulcerative condition of the soft tissues was found to have been aided by a regimen of reduced walking activity and wearing of shoes fitted with the described soles of this invention.

Thus, there has been shown and described a novel therapeutic weight dispersing shoe sole which demonstrates all the objects and advantages sought therefor. It will be apparent to those skilled in the art after reviewing this description, however, that many changes, modifications, variations and other uses and applications for the subject therapeutic weight dispersing shoe sole in addition to those which have been disclosed are possible and contemplated, and all such changes, modifications, variations and other uses and applications which do not depart from the spirit and scope of the invention are deemed to be covered by the invention which is limited only by the claims which follow.

What is claimed is:

1. In a shoe for relieving point pressure or stress on the plantar surfaces of the human foot and having a shoe upper and a shoe sole, the improvement consisting essentially of:
   (a) a width extended sole member underlying substantially the forward half of the shoe sole and projecting laterally at its widest point at least ½ inch (1.25 cm) beyond the sides of said shoe sole and extending forwardly from posteriorly of the metatarsal heads area of the foot to the toe of said shoe sole, the projecting portions being inwardly curved at each of the forward and rearward ends thereof so as to register with the vertical plane of the outer edges of said shoe sole,
   (b) longitudinally extending support members underlying and of substantially the same width as and shorter than each of the medial and lateral projecting portions of said extended sole member, the forward and rearward ends of said support members being tapered forwardly and rearwardly respectively, said support member being fixedly joined to said extended sole member and said extended sole member being fixedly joined to said shoe sole, and
   (c) a heel lift member underlying substantially the full area of and fixedly joined to the heel portion of said shoe.

2. The shoe of claim 1 wherein the thickness of said extended sole member is tapered in the forward portion thereof to a thickness at the forward end of not more than ½ the thickness of the central portion thereof and at the rear end thereof is tapered at an obtuse angle to the rearward half of said shoe sole.

3. The shoe of claim 1 wherein the outer edge of each of said support members is in vertical registry with the outer edge of the projecting portions of said extended sole member and the inner edge of each of said support members is in vertical registry with the respective outer edge of said shoe sole.

4. The shoe of claim 1 wherein the thickness of said heel lift is uniform over the area thereof and ranges in thickness from less than the thickness of said extended sole member to a thickness of at least as great as the total thickness of said extended sole member and said support member.

5. The shoe of claim 1 wherein said extended sole member and said support members are integrally formed as a one-piece construction.

6. The shoe of claim 1 wherein said extended sole member, said support members and said heel lift are integrally formed as a one-piece construction.

7. A shoe sole for fixedly joining to a shoe which shoe has sole and heel portions for relieving point pressure and stress on the plantar surfaces of the human foot consisting essentially of;
   (a) a laterally extended sole member adapted to underlie substantially the forward half of said sole and project at its widest point at least ½ inch (1.25 cm) on at least a portion of both the medial and lateral sides thereof beyond the sole of said shoe and extend forwardly from posteriorly of the metatarsal heads area of the foot to the toe of said sole, the resulting projecting portions inwardly curved at each of the forward and rearward end portions thereof so as to be in vertical registry with the outer edges of the sole of said shoe,
   (b) a longitudinally extending support member underlying at least the widest portion and of substantially the same width as and fixedly joined to each of the medial and lateral projecting portions of said extended sole member, said support member being tapered in thickness at the forward and rearward ends thereof, and
   (c) a heel lift underlying substantially the full area of the heel portion of said shoe.

8. The shoe sole of claim 7 wherein said heel lift, said extended sole member and said underlying support members are integrally formed as a one-piece construction.

9. The shoe sole of claim 7 wherein the thickness of the forward portion of said extended sole member is tapered to not more than about ½ the thickness of the central portion thereof.

10. The shoe sole of claim 7 wherein the outer edges of said support members are in vertical registry with the outer edges of said projecting portions of said extended sole member.

11. The shoe sole of claim 7 wherein the uniform thickness of said heel lift over the area thereof ranges from less than the thickness of said extended sole member to a thickness at least as great as the total thickness of said extended sole member and said support member.

* * * * *